United States Patent
Crotts et al.

(10) Patent No.: US 10,537,638 B2
(45) Date of Patent: Jan. 21, 2020

(54) LOW CONCENTRATION ANTIBODY FORMULATIONS

(71) Applicant: GLAXOSMITHKLINE INTELLECTUAL PROPERTY (NO. 2) LIMITED, Brentford, Middlesex (GB)

(72) Inventors: George Crotts, King of Prussia, PA (US); Sorina Morar-Mitrica, King of Prussia, PA (US)

(73) Assignee: GLAXOSMITHKLINE INTELLECTUAL PROPERTY (NO.2) LIMITED, Brentford, Middlesex (GB)

( * ) Notice: Subject to any disclaimer, the term of this patent is extended or adjusted under 35 U.S.C. 154(b) by 362 days.

(21) Appl. No.: 14/775,900

(22) PCT Filed: Mar. 13, 2014

(86) PCT No.: PCT/IB2014/059757
§ 371 (c)(1),
(2) Date: Sep. 14, 2015

(87) PCT Pub. No.: WO2014/141152
PCT Pub. Date: Sep. 18, 2014

(65) Prior Publication Data
US 2016/0000916 A1    Jan. 7, 2016

Related U.S. Application Data

(60) Provisional application No. 61/787,709, filed on Mar. 15, 2013.

(51) Int. Cl.
| | | |
|---|---|---|
| *A61K 39/395* | (2006.01) | |
| *C07K 16/28* | (2006.01) | |
| *A61K 47/18* | (2017.01) | |
| *A61K 47/26* | (2006.01) | |
| *A61K 9/00* | (2006.01) | |

(52) U.S. Cl.
CPC ...... *A61K 39/39591* (2013.01); *A61K 9/0019* (2013.01); *A61K 47/183* (2013.01); *A61K 47/26* (2013.01); *C07K 16/2809* (2013.01); *C07K 2317/24* (2013.01); *C07K 2317/41* (2013.01); *C07K 2317/52* (2013.01)

(58) Field of Classification Search
None
See application file for complete search history.

(56) References Cited

U.S. PATENT DOCUMENTS

| 7,989,665 B2 | 8/2011 | Saudan et al. |
|---|---|---|
| 2003/0104996 A1 | 6/2003 | Li et al. |

FOREIGN PATENT DOCUMENTS

| EP | 2629889 | 8/2013 |
|---|---|---|
| WO | WO 2003032913 A2 | 4/2003 |
| WO | WO 2003/039485 A2 | 5/2003 |
| WO | WO2006/096461 | * 3/2006 |
| WO | WO 2006/096461 A2 | 9/2006 |
| WO | WO 2006096488 A3 | 11/2006 |
| WO | WO 2007/033230 A2 | 3/2007 |
| WO | WO 2009/070642 A1 | 6/2009 |
| WO | WO 2011008770 A2 | 1/2011 |
| WO | WO 2011/089062 A2 | 7/2011 |
| WO | WO 2011/163566 A2 | 12/2011 |
| WO | WO 2013003680 A1 | 1/2013 |
| WO | WO 2014/141152 A2 | 9/2014 |

OTHER PUBLICATIONS

Bee, Jared S., et al, "Effects of Surfaces and Leachables on the Stability of Biopharmaceuticals", Journal Of Pharmaceutical Sciences, vol. 11, No. 10, Oct. 2011, pp. 4158-4170.
Mahler Hanns-Christian, et al., Surface Activity of a Monoclonal Antibody, Journal od Pharmaceutical Sciences, vol. 98, No. 12, Dec. 2009. pp. 4525-4533.
Bee, Jared S., et al, "Effects of Surfaces and Leachables on the Stability of Biopharmaceuticals", Journal of Pharmaceutical Sciences, vol. 100, No. 10, Oct. 2011, pp. 4158-4170.
Couston, Ruairidh G., et al., "Adsorption behavior of a human monoclonal antibody at hydrophilic and hydrophobic surfaces", MABS, vol. 5, No. I, Jan. 2013, pp. 126-139.
Deechongkit, Songpon, et al., "Physical and Biophysical Effects of Polysorbate 20 and 80 on Darbepoetin Alfa", Journal of Pharmaceutical Sciences, vol. 98, No. 9, Sep. 2009, pp. 3200-3217.
Hyo, Jin Lee, et al., "Molecular origins of surfactant-mediated stabilization of protein drugs", Advanced Drug Delivery Reviews, Elsevier, Amsterdam, NL, vol. 63, No. 13, Jun. 29, 2011, pp. 1160-1171.
Mahler Hanns-Christian, et al. "Adsorption Behavior of a Surfactant and a Monoclonal Antibody to Sterilizing-Grade Filters", Journal of Pharmaceutical Sciences, vol. 99, No. 6, Jun. 2010, pp. 2620-2627.
Mahler Hanns-Christian, et al., Surface Activity of a Monoclonal Antibody, Journal of Pharmaceutical Sciences, vol. 98, No. 12, Dec. 2009, pp. 4525-4533.
Pinholt, Charlotte et al., "The importance of interfaces in protein drug delivery why is protein adsorption of interest in pharmaceutical formulations?", Expert Opinion on Drug Delivery, Informa Healthcare, UK, vol. 8, No. 7, Jul. 1, 2011, pp. 949-964.

(Continued)

*Primary Examiner* — Yunsoo Kim
(74) *Attorney, Agent, or Firm* — Donald Huddler; Duke M. Fitch; Edward R. Gimmi

(57) ABSTRACT

The present invention is directed formulations for low concentrations of therapeutic proteins and methods of making the same. In one aspect the present invention is directed to a formulation for a therapeutic protein comprising: a) the therapeutic protein; and b) a surfactant; wherein the molar ratio of surfactant to therapeutic protein is at least 100. In another aspect the present invention is directed to a formulation for a therapeutic protein comprising: a) the therapeutic protein; and b) an antioxidant, wherein the molar ratio of antioxidant to therapeutic protein is at least 750.

14 Claims, 6 Drawing Sheets
Specification includes a Sequence Listing.

(56) References Cited

OTHER PUBLICATIONS

Muriel Paul et al., "Long-term stability of diluted solutions of the monoclonal antibody rituximab", *International Journal of Pharmaceutics*, 436(1-2): 282-290 (2012).
Muriel Paul, et al.,"Long-term physico-chemical stability of diluted trastuzumab", *International Journal of Pharmaceutics*, 448(1):101-104 (2013).
Wei Wang, et al., "Dual effects of Tween 80 on protein stability", *International Journal of Pharmaceutics*, 347(1-2):31-38 (2008).
Agarkhed, et al., Effect of Polysorbate 80 Concentration on Thermal and Photostability of a Monoclonal Antibody, *AAPS PharmaSciTech*, 14(1):1-9 (2012).
Lene Jorgensen, et al., Recent trends in stabilizing peptides and proteins in pharmaceutical formulation—considerations in the choice of excipients, *Expert Opinion on Drug Delivery*, 6(11):1219-1230 (2009).
Sorina Morar-Mitrica, et al., *Development of a stable low-dose aglycosylated antibody formulation to minimize protein loss during intravenous administration*, mAbs, 7(4):792-803 (2015).
Wang Wei., Instability, stabilization and formulation of liquid protein pharmaceuticals, *Intl Journal of Pharmaceutics*, 185(2):129-188 (1999).
Wang W., et al., Antibody Structure, Instability and Formulation, *Journal of Pharmaceutical Sciences*, 96(1):1-26 (2007).

\* cited by examiner

Figure 5 depicts Otelixizumab Heavy Chain Amino Acid Sequence (SEQ ID NO: 1).

```
EVQLLESGGG LVQPGGSLRL SCAASGFTFS SFPMAWVRQA PGKGLEWVST
ISTSGGRTYY RDSVKGRFTI SRDNSKNTLY LQMNSLRAED TAVYYCAKFR
QYSGGFDYWG QGTLVTVSSA STKGPSVFPL APSSKSTSGG TAALGCLVKD
YFPEPVTVSW NSGALTSGVH TFPAVLQSSG LYSLSSVVTV PSSSLGTQTY
ICNVNHKPSN TKVDKKVEPK SCDKTHTCPP CPAPELLGGP SVFLFPPKPK
DTLMISRTPE VTCVVVDVSH EDPEVKFNWY VDGVEVHNAK TKPREEQYAS
TYRVVSVLTV LHQDWLNGKE YKCKVSNKAL PAPIEKTISK AKGQPREPQV
YTLPPSRDEL TKNQVSLTCL VKGFYPSDIA VEWESNGQPE NNYKTTPPVL
DSDGSFFLYS KLTVDKSRWQ QGNVFSCSVM HEALHNHYTQ KSLSLSPGK
```

Figure 6 depicts Otelixizumab Light Chain Amino Acid Sequence (SEQ ID NO: 2).

```
DIQLTQPNSV STSLGSTVKL SCTLSSGNIE NNYVHWYQLY EGRSPTTMIY
DDDKRPDGVP DRFSGSIDRS SNSAFLTIHN VAIEDEAIYF CHSYVSSFNV
FGGGTKLTVL RQPKAAPSVT LFPPSSEELQ ANKATLVCLI SDFYPGAVTV
AWKADSSPVK AGVETTTPSK QSNNKYAASS YLSLTPEQWK SHRSYSCQVT
HEGSTVEKTV APTECS
```

LOW CONCENTRATION ANTIBODY FORMULATIONS

This application is a 371 of International Application No. PCT/IB2014/059757, filed 13 Mar. 2014, which claims the benefit of U.S. Provisional Application No. 61/787,709, filed 15 Mar. 2013, which are incorporated herein in their entirety.

FIELD OF THE INVENTION

The present invention relates to the field of formulations for therapeutic proteins. More specifically, the invention relates to formulations for low concentrations of therapeutic proteins and methods of making the same.

BACKGROUND OF THE INVENTION

A number of biopharmaceuticals are formulated and provided ready for clinical administration without further manipulation, however, many products require varying degrees of handling by the nurse, pharmacist, or physician. During handling and administration, physical and chemical stability of the protein must be maintained. Loss of stability can occur when the protein formulation is diluted to low concentrations with intravenous (i.v.) solutions, thus lowering the excipient concentration and modifying the composition and properties of the original drug product formulation. When delivering a biopharmaceutical product via the i.v. route several factors must be considered including protein properties, formulation composition, concentration of the active product to be delivered, choice of diluent, contact surfaces, and infusion time and rate. The contact surface is of particular interest as proteins tend to absorb at interfaces due to their amphiphilic nature. With the widespread use of a variety of plastic polymers in syringes and i.v. infusion containers and lines, the risk of protein loss by adsorption is significant, especially at low concentrations (<0.5 mg/mL). Thus, protein loss due to adsorption onto filters, containers, syringes, and tubing must be investigated and addressed during drug product development, particularly for low dose products.

The present invention provides formulations suitable for low concentration therapeutic proteins.

SUMMARY OF THE INVENTION

In one aspect the present invention is directed to a formulation for a therapeutic protein comprising: a) the therapeutic protein; and b) a surfactant; wherein the molar ratio of surfactant to therapeutic protein is at least 100.

In another aspect the present invention is directed to a formulation for a therapeutic protein comprising: a) the therapeutic protein; and b) an antioxidant, wherein the molar ratio of antioxidant to therapeutic protein is at least 750.

BRIEF DESCRIPTION OF THE DRAWINGS

FIG. 5 depicts Otelixizumab Heavy Chain Amino Acid Sequence (SEQ ID NO: 1).

FIG. 6 depicts Otelixizumab Light Chain Amino Acid Sequence (SEQ ID NO: 2).

DETAILED DESCRIPTION OF THE INVENTION

Figure 1:
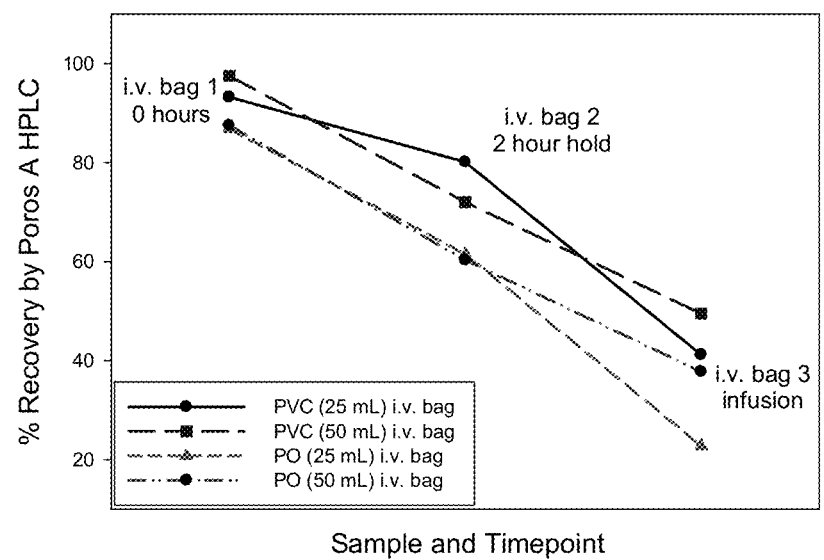
FIG. 1 depicts Percent (%) average recovery results, as measured via Poros A-HPLC analysis.

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a sugar" includes a combination of two or more sugars, and the like.

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

In one aspect the present invention is directed to a formulation for a therapeutic protein comprising: a) the therapeutic protein; and b) a surfactant; wherein the molar ratio of surfactant to therapeutic protein is at least 100.

In certain embodiments the molar ratio of surfactant to therapeutic protein is selected from the group consisting of at least 150, at least 200, at least 250, at least 300, at least 400, and at least 500. In one embodiment the molar ratio of surfactant to therapeutic protein is about 545.

In certain embodiments the surfactant is selected from the group consisting of polysorbate-20, polysorbate-40, polysorbate-60, polysorbate-65, polysorbate-80, polysorbate-85, poloxamer 188, and combinations thereof. In one embodiment the formulation comprises about 0.01% w/v to about 0.5% w/v surfactant. In one embodiment the is about 0.1% w/v, about 0.2% w/v, about 0.3% w/v, about 0.4% w/v, or about 0.5% w/v surfactant. In one embodiment the formulation comprises about 0.1% w/v polysorbate 80.

In one aspect the present invention is directed to a formulation for a therapeutic protein comprising: a) the therapeutic protein; and b) an antioxidant, wherein the molar ratio of antioxidant to therapeutic protein is at least 750.

In certain embodiments the molar ratio of antioxidant to therapeutic protein is selected from the group consisting of at least 1000, at least 1250, at least 1500, at least 2000, at least 2500, at least 3000, at least 3500, at least 4000, at least 4500, at least 5000, at least 5500, at least 6000, at least 6500, and at least 7000. In one embodiment the molar ratio of antioxidant to therapeutic protein is about 7143. In certain embodiments the antioxidant is selected from the group consisting of methionine, cysteine, glutathione, and monothioglycerol. In other embodiments the antioxidant is a metal chelator. Metal chelators include, but are not limited to ethylenediaminetetraacetate ("EDTA"), ethylene glycol tetraacetic acid ("EGTA"), (thiamine tetrahydrofurfuryl disulfide ("TTFD"), and 2,3-dimercaptosuccinic acid ("DMSA"). In certain embodiments the formulation comprises about 1 mM to about 50 mM antioxidant. In one embodiment the formulation comprises about 5 mM, about 10 mM, about 15 mM, about 20 mM, about 25 mM, about 30 mM, about 35 mM, about 40 mM, or about 45 mM antioxidant. In one embodiment the formulation comprises about 10 mM methionine.

In certain embodiments the formulation further comprises a buffer, wherein the pH of the formulation is about 4.0 to about 8.0. In certain embodiments the pH of the formulation is about 4.0, about 4.5, about 5.0, about 5.5, about 6.0, about 6.5, about 7.0, about 7.2 about, 7.5, or about 8.0. In one embodiment the buffer is selected from the group consisting of histidine, acetate, succinate, and citrate. In certain embodiments the formulation comprises about 1 mM to about 100 mM buffer. In one embodiment the formulation comprises about 10 mM, about 20 mM, about 30 mM, about 40 mM, about 50 mM, about 60 mM, about 70 mM, about 80 mM, about 90 mM, or about 100 mM buffer. In one embodiment the formulation comprises about 20 mM histidine, at about pH 6.5.

In certain embodiments the therapeutic protein is an antigen binding protein. In one embodiment the antigen binding protein is an antibody or a fragment thereof. In one embodiment the antigen binding protein is an immunoglobulin single variable domain. In one embodiment the antigen binding protein binds to human CD3. In one embodiment the antigen binding polypeptide is an anti-CD3 antibody. In one embodiment the anti-CD3 antibody comprises a heavy chain comprising SEQ ID NO:1 and a light chain comprising SEQ ID NO:2.

In certain embodiments the therapeutic protein is present at a concentration of about 0.01 mg/ml to about 1 mg/ml. In one embodiment the therapeutic protein is present at a concentration of about 0.1 mg/ml to about 0.5 mg/ml. In one embodiment the therapeutic protein is present at a concentration of about 0.2 mg/ml.

In one embodiment the formulation is a reconstituted formulation. In one embodiment the formulation is a liquid pharmaceutical formulation. In one embodiment the formulation is suitable for parenteral administration.

In one aspect the present invention is directed to a formulation for a therapeutic protein comprising: a) the therapeutic protein; and b) about 0.01% w/v to about 0.5% w/v surfactant, wherein the molar ratio of surfactant to therapeutic protein is at least 100; c) about 1 mM to about 50 mM antioxidant, wherein the molar ratio of antioxidant to therapeutic protein is at least 750; and d) about 1 mM to about 100 mM buffer, wherein the pH of the formulation is about 4.0 to about 8.0.

In one embodiment the formulation further comprises about 0.01 mM to about 1.0 mM EDTA. In certain embodiments the formulation comprises about 0.05 mM, about 0.1 mM, about 0.15 mM, about 0.2 mM, 0.25 mM, about 0.3 mM, about 0.35 mM, about 0.4 mM, 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, or about 1.0 mM EDTA. In one embodiment the formulation comprises about 0.05 mM EDTA.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine: D-p-fluorophenylalanine; D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

"Recombinant" when used with reference to a protein indicates that the protein has been modified by the introduction of a heterologous nucleic acid or protein or the alteration of a native nucleic acid or protein.

As used herein a "therapeutic protein" refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount"

means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

All "amino acid" residues identified herein are in the natural L-configuration. In keeping with standard polypeptide nomenclature, abbreviations for amino acid residues are as follows:

| 1 Letter | 3 Letter | Amino Acid |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

In another embodiment the polypeptide is an antigen binding polypeptide. In one embodiment the antigen binding polypeptide is selected from the group consisting of a soluble receptor, antibody, antibody fragment, immunoglobulin single variable domain, Fab, F(ab')2, Fv, disulphide linked Fv, scFv, closed conformation multispecific antibody, disulphide-linked scFv, or diabody.

The term "antigen binding polypeptide" as used herein refers to antibodies, antibody fragments and other protein constructs which are capable of binding to an antigen.

The terms Fv, Fc, Fd, Fab, or F(ab)2 are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see for example EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAbs (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain.

As used herein, the term "antigen-binding site" refers to a site on a protein which is capable of specifically binding to antigen, this may be a single domain, for example an epitope-binding domain, or it may be paired $V_H/V_L$ domains as can be found on a standard antibody. In some aspects of the invention single-chain Fv (ScFv) domains can provide antigen-binding sites.

The terms "mAbdAb" and "dAbmAb" are used herein to refer to antigen-binding proteins of the present invention. The two terms can be used interchangeably, and are intended to have the same meaning as used herein.

In another embodiment the formulation further comprises additional excipients. "Excipients" includes, but is not limited to, stabilizers, for example, human serum albumin (hsa), bovine serum albumin (bsa), α-casein, globulins, α-lactalbumin, LDH, lysozyme, myoglobin, ovalbumin, RNase A; buffering agents, for example, citric acid, HEPES, histidine, potassium acetate, postassium citrate, potassium phosphate ($KH_2PO_4$), sodium acetate, sodium bicarbonate, sodium citrate, sodium phosphate ($NAH_2PO_4$), Tris base, and Tris-HCl; amino acids/metabolites, for example, glycine, alanine (α-alanine, β-alanine), arginine, betaine, leucine, lysine, glutamic acid, aspartic acid, histidine, proline, 4-hydroxy-proline, sarcosine, γ-aminobutyric acid (GABA), opines (alanopine, octopine, strombine), and trimethylamine N-oxide (TMAO); surfactants, for example, polysorbate 20 and 80, and poloxamer 407: lipid molecules, for example, phosphatidyl choline, ethanolamine, and acethyltryptophanate: polymers, for example, polyethylene glycol (PEG), and polyvinylpyrrolidone (PVP) 10, 24, 40; low molecular weight excipients, for example, arabinose, cellobiose, ethylene glycol, fructose, fucose, galactose, glycerin/glycerol, glucose, inositol, lactose, maltose, maltotriose, mannose, melibiose, 2-methyl-2,4-pentanediol, octulose, propylene glycol, raffinose, ribose, sucrose, trehalose, xylitol, and xylose; and high molecular weight excipients, for example, cellulose, β-cyclodextrin, dextran (10 kd), dextran (40 kd), dextran (70 kd), ficoll, gelatin, hydroxypropylmethyl-cellulose, hydroxyethyl starch, maltodextrin, methocel, peg (6 kd), polydextrose, polyvinylpyrrolidone (PVP) k15 (10 kd), PVP (40 kd), PVP k30 (40 kd), PVP k90 (1000 kd), sephadex G 200, and starch; antioxidants, for example, ascorbic acid, cysteine HCl, thioglycerol, thioglycolic acid, thiosorbitol, and glutathione; reducing agents, for example, cysteine HCl, dithiothreotol, and other thiol or thiophenes; chelating agents, for example, EDTA, EGTA, glutamic acid, and aspartic acid; inorganic salts/metals, for example, $Ca^{2+}$, $Ni^{2+}$, $Mg^{2+}$, $Mn^{2+}$, $Na_2SO_4$, $(NH_4)_2SO_4$, $Na_2HPO_4/NaH_2PO_4$, $K_2HPO_4/KH_2PO_4$, $MgSO_4$, and NaF; organic salts, for example, Na acetate, Na polyethylene, Na caprylate (Na octanoate), proprionate, lactate, succinate, and citrate; organic solvents, for example, acetonitrile, dimethylsulfoxide (dmso), and ethanol.

In one embodiment the formulation is formulated to a pH of about 4.0 to about 8.0. In one embodiment the formulation is formulated to a pH of about 6.5. In one embodiment the formulation comprises about 10 mM to about 50 mM histidine. In one embodiment the formulation comprises about 20 mM histidine.

The agents used to stabilize the therapeutic protein can be added at any stage of the formulation process. For example, before, after, or concurrently with the buffer, the therapeutic protein, or with any excipients.

The formulations of the present invention may be administered by any suitable route of administration, including systemic administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion Inhalation refers to administration into the patient's lungs whether inhaled through the mouth or through the nasal passages.

The present invention is also directed to a stable formulation produced by any of the methods of the present invention.

EXAMPLES

Example 1—Otelixizumab is a Low Concentration-Low Dose mAb

Otelixizumab is a humanized mAb (IgG1) directed against human CD3 with no glycosylation site in the Fc domain. In order to facilitate the accurate preparation and administration of clinical doses (0.1 to 0.5 mg per day), the drug product was developed at a concentration of 0.2 mg/mL with different vial unit presentations corresponding to the varying daily doses. The dose administration required dilution of the mAb in an i.v. bag containing isotonic 0.9% sodium chloride (saline), and delivery of the entire bag contents via a standard infusion pump. This dosing methodology led to protein concentrations in the i.v. bag as low as 2 µg/mL. As a direct consequence, the risk of significant protein loss was very high. For this reason, short-term stability and compatibility studies with commercially-relevant i.v. giving sets were performed to assess the feasibility of administering the existing product, as well as, to develop an alternative formulation that would support the proposed dilution and administration design intent.

Example 2—Assessment of Unacceptable mAb Loss During in-Use Stability Studies A stability study was conducted to assess the feasibility of administering the 0.2 mg/mL formulation comprised of histidine buffer only using commercially-available i.v. giving sets. A drug product volume equivalent to the target dose (0.1 mg) was added to an i.v. saline bag, and the stability of the diluted product was assessed. Relatively low saline volumes of either 25 or 50 mL were selected to minimize potential protein losses due to adsorption, resulting in active concentrations in the i.v. bags of 4 and 2 µg/mL, respectively. In addition, i.v. bags constructed of two different types of materials (polyolefin, PO and polyvinylchloride, PVC) were evaluated. The bags were placed on the laboratory bench and exposed to ambient temperature and lighting conditions. Three sets of bags were prepared for each test configuration: bag 1 served as a test of the initial condition, bag 2 reflected a hold, and bag 3 was used to simulate a clinical preparation and infusion of the protein solution through an i.v. line with in-line filter (B. Braun Horizon Pump Filtered i.v set). Bags were prepared and tested in duplicates. Samples were collected and tested immediately after the i.v. bag preparation (0 hours hold in the i.v. bag), and following a 2-hour hold in the i.v. bag. Additional samples were collected following a 2-hour infusion through the i.v. line. Polysorbate 80 (PS80) was added to all retain samples at a final concentration of 0.001% to prevent loss via adsorption within the collection tubes. Percent (%) average recovery results were measured via Poros A-HPLC analysis. Recoveries were calculated based on target concentrations in the bag, and the reported values were the average of two different preparations.

Percent (%) average recovery results, as measured via Poros A-HPLC analysis, are plotted in FIG. 1. The recoveries in all PO bags (range of 23% to 88%) trended lower than those in PVC bags (range of 41% to 98%). Overall, the losses in all test systems after room temperature storage for 2 hours were well above 10%. Furthermore, greater than 50% of the protein was lost when the product was infused through an i.v. line and filter, regardless of bag material.

Example 3—Optimization of Surfactant Concentration in i.v. Bags to Improve Stability Against Loss Via Adsorption During Administration Due to unacceptable protein recovery upon administration of the mAb formulated in histidine buffer alone, a second study was carried out to determine whether incorporating the surfactant polysorbate 80 (PS80) into the formulation could enable the delivery of ≥90% of the dose. Thus, the preparation and infusion of 0.1 mg protein was tested using a PO bag containing 50 mL saline (2 µg/mL mAb), in combination with an i.v. line with an in-line filter. Only the PO bag was studied as the initial results showed lower recoveries in PO bags when compared to those in PVC bags, indicating that the PO bag may represent the more difficult hurdle to demonstrate acceptable protein recovery.

A similar experimental design was used in this second study, as follows: mAb stock solutions at 0.2 mg/mL concentration and containing various PS80 concentrations (0.02, 0.05, 0.1, and 0.3% w/v) were prepared fresh, and added to i.v. infusion bags (PO only) as described above. The final mAb concentration in the i.v. saline bag was 2 µg/mL, and the final surfactant concentrations were 0.0002, 0.0005, 0.001, and 0.003%. Additional PS80 (to a final concentration of at least 0.001%) was added to all samples before analysis. The i.v. line tested was a Baxter Continu-Flo Solution Set with filter. The mAb concentration was measured at initial and following either a 2-hour hold in the i.v. bag or infusion through the selected i.v. line. The recovery results were determined via Poros A-HPLC analysis. Recoveries were calculated based on target concentrations in the bag, and the reported values were the average of two different preparations.

Figure 2:
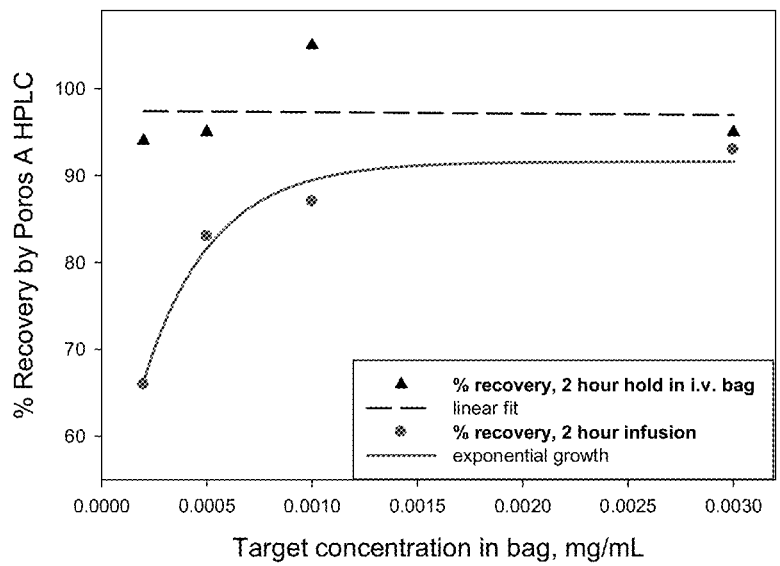
FIG. 2 depicts the average % recoveries, as determined via Poros A-HPLC analysis.

The average % recoveries, as determined via Poros A-HPLC analysis, are plotted in FIG. 2. Depending on the test condition, the measured values ranged from 66% to 105%. Approximately 95% protein recoveries at all test PS80 concentrations were observed in the i.v. bags during the 2-hour hold. Thus, PS80 concentrations as low as 0.0002% in the bag (equivalent to 0.02% in the drug product formulation) were sufficient to inhibit adsorption-mediated loss of the mAb. However, there is an additional, significant loss on the i.v. line and filter, as shown in FIG. 2. The dependency of total protein loss on surfactant concentration appeared to be non-linear, with close to 90% recovery attained at PS80 concentrations at or higher than 0.001% in a 50 mL i.v. bag (or 0.1% in the product).

Example 4—Stability of the PS80-Containing Product: Evaluating the Oxidation Risk Protein stability under accelerated conditions has conventionally been employed in biopharmaceutical development to select the optimum formulation for long-term storage as well as to provide a prediction of shelf life. Here, a short term (2 week) accelerated stability study was conducted at 40° C. to evaluate the stability of the PS80-containing formulation, specifically to assess the risk that PS80 may adversely impact the stability of the mAb via oxidative degradation during long-term storage.

The target formulations were prepared by diluting the mAb drug substance with various a PS80 stock solution prepared in histidine buffer. The final mAb concentration in each vial was 0.2 mg/mL. Each test condition was aliquoted into glass vials, and the vials were stored at 40° C. for 2 weeks. The analytical testing included size exclusion chromatography ("SEC"), capillary isoelectric focusing ("cIEF"), and mass spectrometry ("MS") analyses.

Oxidation of the methionine residues leads to the formation of methionine sulfoxide and a mass shift of 16 Da which can be detected using MS. MS was used to compare relative amounts of oxidized and unoxidized peptides. The MS results are included in Table 1. For mAb control sample (in buffer with no excipients), the measured % oxidation at the tested methionine residues was as high as 11%. When the surfactant is present in the formulation, a significantly increased level of mAb oxidation (up to 30%) at the two most exposed methionine residues was observed. This increase in % oxidation is predictive of decreased long-term stability as oxidation can further lead to aggregation and other secondary degradation processes.

TABLE 1

| Sample | Condition | SEC | | cIEF | | MS | |
|---|---|---|---|---|---|---|---|
| | | % LMW % HMW | % Monomer | # peaks pI Main | % Basic % Main | % oxidation at Met254 | % oxidation Met430 |
| 0.2 mg/ml mAb in 20 mM His buffer | 5° C. 2 weeks | | | 6 8.5 | 17.2 12.0 70.9 | | |
| | 40° C. 2 weeks | 1.2 0.4 | 98.4 | 7 8.5 | 32.0 10.3 57.7 | 11.1 | 3.8 |
| 0.2 mg/ml mAb in 20 mM His buffer + 0.1% PS80 | 5° C. 2 weeks | | | 6 8.5 | 17.4 10.4 72.2 | | |
| | 40° C. 2 weeks | 1.4 0.8 | 97.8 | 7 8.5 | 34.0 10.6 55.5 | 29.6 | 14.0 |

Example 5—Increased Stability of the PS80-Containing Product in the Presence of Selected Antioxidants Additional work was further conducted to screen excipients that would improve the chemical stability of the mAb in the proposed formulation containing 0.1% PS80. Five different antioxidants (including free radical scavengers and one metal chelator) were tested.

The target formulations were prepared by diluting the mAb drug substance with various excipient stock solutions prepared in histidine buffer, as follows: PS80 (polysorbate 80); Met (methionine); Cys (cysteine); Glut (glutathione); MTG (monothioglycerol); EDTA (edetate disodium). The final antioxidant concentrations in the product vial were: 5 mM Met, 5 mM Cys, 5 mM Glut, 5 mM MTG, and 1 mM EDTA. The final mAb concentration in each vial was 0.2 mg/mL. Each test condition was aliquoted into glass vials, and the vials were stored at 40° C. for 2 weeks. The analytical testing included cIEF and MS analyses.

As seen in Table 2, all antioxidants were able to attenuate the negative stability impact of the surfactant. The data show the lowest extent of oxidation in the formulation containing methionine. Although EDTA seemed to be less effective than Met at controlling oxidation, it still significantly reduced the extent of PS80-dependent oxidation by almost 4-fold.

Table 2 also presents the results of charge analysis via capillary isoelectric focusing (cIEF) analysis. The largest values for % Main were observed for the control formulation containing no antioxidants, and also for the PS80-containing formulations which also included either Met or EDTA. As evaluated by using cIEF, the least stable formulations contained Cys, Glut, or MTG.

TABLE 2

Stability of 0.2 mg/mL mAb formulated with 0.1% PS80 and various antioxidants: results of MS and cIEF analysis following storage in vials for 2 weeks at 40° C.

| 0.2 mg/mL mAb formulated with: | MS | | cIEF | | |
|---|---|---|---|---|---|
| | % oxidation at methionine residue 254 | % oxidation at methionine residue 430 | % Acidic peaks | % Basic peaks | % Main peak |
| Buffer control (No excipients) | 11.1 | 3.8 | 32.0 | 10.3 | 57.7 |
| 0.1% PS80 | 29.6 | 14.0 | 34.0 | 10.6 | 55.5 |
| 0.1% PS80 5 mM Met | 3.7 | 1.1 | 32.6 | 9.9 | 57.6 |
| 0.1% PS80 5 mM Cys | 5.3 | 1.2 | 35.9 | 9.4 | 54.8 |
| 0.1% PS80 5 mM Glut | 11.6 | 3.6 | 43.1 | 8.2 | 48.8 |
| 0.1% PS80 5 mM MTG | 5.9 | 1.4 | 36.6 | 10.4 | 53.2 |
| 0.1% PS80 1 mM EDTA | 7.6 | 1.8 | 29.2 | 10.9 | 59.9 |

Figure 3:
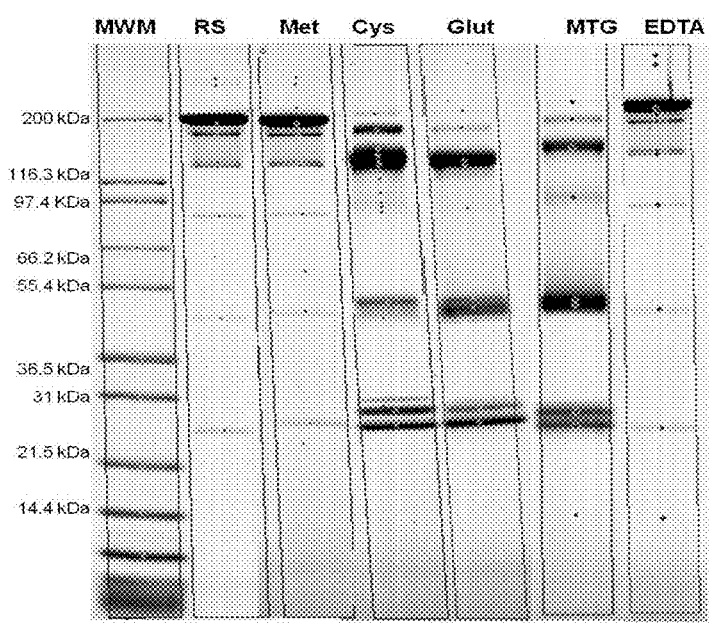
FIG. 3 depicts non-reducing SDS-PAGE for mAb samples formulated with different antioxidants and stored for 2 weeks at 40° C. (lanes from different gels were combined to better illustrate the differences observed in each sample containing antioxidants).

To help explain the discrepancies between the MS and cIEF results, SDS-PAGE analysis was also performed. The SDS-PAGE results for the formulations containing Cys, Glut, or MTG showed a significant shift of bands in the non-reduced gel for the samples stored at 40° C. for 2 weeks (FIG. 3), indicative of chemical degradation via disulfide shuffling. The chemical instability of the mAb in the presence of Cys, Glut, or MTG as detected by SDS-PAGE correlated nicely with the increase in the acidic peaks by cIEF (Table 2). Thus, Met and EDTA were the only tested antioxidants that showed no disruption of the disulfide bond pattern in the product, and were confirmed to have optimum antioxidant activity. The overall product stability in formulations containing antioxidants can be ranked as: Met>EDTA>>Cys, Glut, MTG.

Example 6—Long-Term Stability of the Reformulated Product and Identification of Functional Antioxidant Levels A development stability study was performed to assess the long-term and accelerated stability of the 0.2 mg/mL mAb formulations containing PS80, Met, and EDTA. A broad range of conditions were tested, including a series of six concentrations of Met ranging from 0 to 40 mM. The EDTA level was fixed at 0.05 mM based on previous experience with mAbs. A total of 8 formulations were placed on stability. A summary of the tested formulations was presented in Table 3. Formulations A-F incorporated Met at 0, 5, 10, 15, 20, and 40 mM, with a fixed level of EDTA (0.05 mM) and PS80 (0.1%). Formulations G and H served as PS80 (only) and buffer alone (no excipients) controls, respectively. Each formulation was aliquoted into glass vials, and the vials were stored inverted at refrigerated (2-8° C., primary) and 25° C. (accelerated) conditions. The mAb concentration in each vial was 0.2 mg/mL. Analytical pulls were planned for 1, 2, 3, and 6 months with results compared to initials.

TABLE 3

| Formula Code | mAb mg/mL | PS80 % | Met mM | EDTA mM |
|---|---|---|---|---|
| A | 0.2 | 0.1 | 0 | 0.05 |
| B | 0.2 | 0.1 | 5 | 0.05 |
| C | 0.2 | 0.1 | 10 | 0.05 |
| D | 0.2 | 0.1 | 15 | 0.05 |
| E | 0.2 | 0.1 | 20 | 0.05 |
| F | 0.2 | 0.1 | 40 | 0.05 |
| G | 0.2 | 0.1 | 0 | 0 |
| H | 0.2 | 0 | 0 | 0 |

Experimental setup of formulation development stability study. The formulation composition pertaining to each formula code is detailed.

Figure 4:
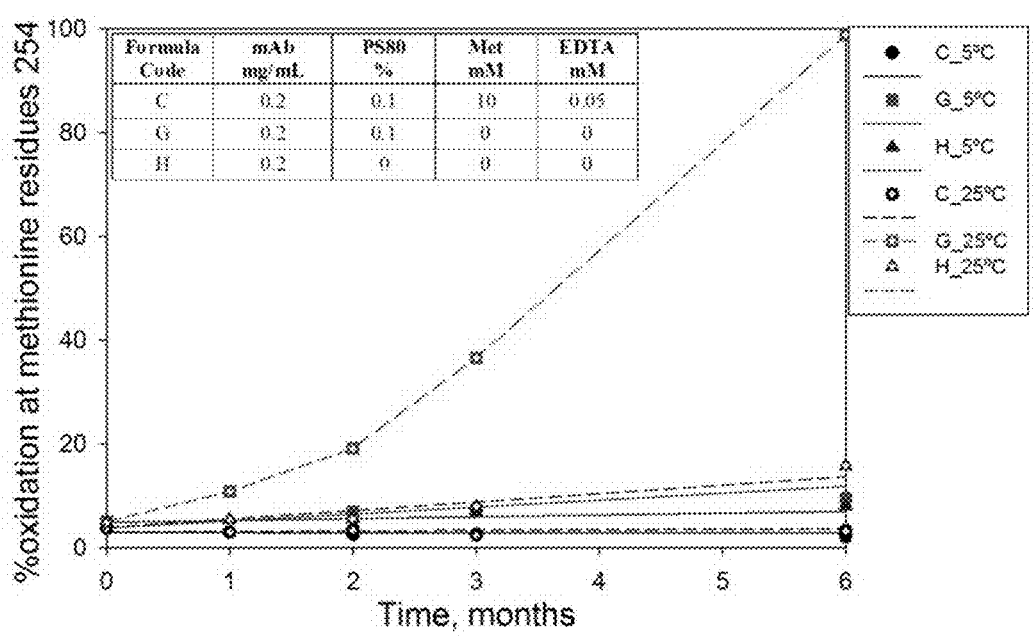
FIG. 4 depicts oxidation trends for mAb stability samples C (containing a surfactant and a combination of two antioxidants), G (containing a surfactant only), and H (no excipient control), stored at 5 and 25° C. for 6 months.

Oxidation levels on stability were measured using MS. Table 4 lists the oxidization levels of methionine residues as determined by MS quantitation following trypsin digestion of the protein and HPLC separation of the resulting peptides. Representative oxidation trends for samples C (PS80, Met, and EDTA), G (PS80 only), and H (no excipients) stored at 2-8° C. and 25° C. for 6 months are plotted in FIG. 4. Oxidation was initially observed in all samples at the (theoretically) most exposed methionine residue 254 (M254). Interestingly, differences between samples were present at initial analysis, with samples G and H showing ~3% oxidation at the second exposed methionine residue 430 (M430). Samples A through F contained at least one antioxidant (Met), while samples G and H did not; thus, these data may not only be representative of stability upon storage, but may be reflective of the degradation during sample preparation and analysis. The protective effect of the combined addition of EDTA and Met was evident in samples B-F, in which both antioxidants were present. Specifically, over a 6-month period at 2-8° C. and 25° C., oxidation at the M254 remained low (≤4.1%), while little or no oxidation was observed at M430. These data testify to the effectiveness of the antioxidant combination.

MS analysis of sample A, containing EDTA without Met, assisted in differentiating various oxidation mechanisms. While oxidation levels in sample A remained slightly lower than in the control sample H (buffer only), and much lower than in the control sample G (PS80), they were higher than those measured in samples B-F containing Met in addition to EDTA. Comparison of control samples G (PS80) and H (buffer, no excipients) was of further critical importance as the corresponding MS results confirmed three previous hypotheses: 1. oxidation is a degradation pathway even in the absence of PS80, 2. oxidation occurs at refrigerated storage, and it is significantly accelerated at increased storage temperatures, 3. the addition of PS80 accelerates the oxidative degradation pathway presumably through both a peroxide- and metal-dependent pathway. Data collected on samples stored for 6 months at 25° C. showed that oxidation reaches the highest levels (100%) in the PS80 control formulation (G), as expected. In addition, the oxidation levels detected in the formulation (H) were significantly higher than in the samples containing the antioxidant combination (A-F). These data indicate that a combination of two antioxidants, Met (a free radical scavenger) and EDTA (a metal chelator) essentially prevents oxidation, and that the quenching mechanism is not temperature dependent.

TABLE 4

| Formula Code/ Timepoint | | % oxidation at methionine residue 254 | | % oxidation at methionine residue 430 | |
|---|---|---|---|---|---|
| | | 2-8° C. | 25° C. | 2-8° C. | 25° C. |
| A | Initial | 3.5 | NQ | NQ | NQ |
| | 1 month | NT | 4.6 | NT | 2.6 |
| | 2 months | 6.9 | 6.6 | 3.6 | 1.7 |
| | 3 months | 6.2 | 10.4 | 2.7 | 5.1 |
| | 6 months | 6.3 | 13.1 | 2.5 | 7.2 |
| B | Initial | 2.3 | NQ | NQ | NQ |
| | 1 month, | NT | 3.8 | NT | NQ |
| | 2 months | 2.6 | 3.3 | NQ | NQ |
| | 3 months | 2.7 | 3.0 | NQ | NQ |
| | 6 months | 2.2 | 2.6 | NQ | NQ |
| C | Initial | 3.7 | NQ | NQ | NQ |
| | 1 month | NT | 3.0 | NT | NQ |
| | 2 months | 2.5 | 3.4 | NQ | NQ |
| | 3 months | 2.5 | 2.4 | NQ | NQ |
| | 6 months | 2.1 | 3.2 | NQ | NQ |
| D | Initial | 2.9 | NQ | NQ | NQ |
| | 1 month | NT | 2.3 | NT | NQ |
| | 2 months | 3.5 | 3.2 | NQ | NQ |
| | 3 months | 2.8 | 2.5 | NQ | NQ |
| | 6 months | 2.0 | 3.4 | NQ | NQ |
| E | Initial | 1.5 | NQ | NQ | NQ |
| | 1 month | NT | 2.5 | NT | NQ |
| | 2 months | 3.2 | 3.3 | NQ | NQ |
| | 3 months | 2.4 | 2.2 | NQ | NQ |
| | 6 months | 2.0 | 2.4 | NQ | NQ |
| F | Initial | 1.7 | NQ | NQ | NQ |
| | 1 month | NT | 3.2 | NT | NQ |
| | 2 months | 2.6 | 3.1 | NQ | NQ |
| | 3 months | 2.1 | 2.2 | NQ | NQ |
| | 6 months | 2.2 | 2.4 | NQ | NQ |
| G | Initial | 5.0 | NQ | 2.6 | NQ |
| | 1 month | NT | 10.8 | NT | 6.1 |
| | 2 months | 6.9 | 19.1 | 3.5 | 11.8 |
| | 3 months | 7.3 | 36.5 | 3.7 | 19.3 |
| | 6 months | 9.5 | 98.8 | 5.3 | 97.3 |
| H | Initial | 4.8 | NQ | 2.8 | NQ |
| | 1 month | NT | 5.4 | NT | 2.7 |
| | 2 months | 3.6 | 5.5 | 1.8 | 2.9 |
| | 3 months | 6.8 | 7.9 | 2.4 | 3.1 |
| | 6 months | 8.0 | 15.7 | 5.6 | 8.2 |

NQ = not quantified
NT = not tested

Results of peptide mapping by MS analysis reported for various methionine residues in otelixizumab stability samples A-H, containing different levels of surfactant, antioxidant, and metal chelator, and following storage for 6 months at various storage temperatures. The formulation composition pertaining to each formula code is described in detail in Table 3.

Example 7—The Composition of Low Concentration/Low Dose Otelixizumab Formulation is a Unique Combination of Two Antioxidants at a High Surfactant Level Table 5, below, is a summary of the composition and excipient function of the low-concentration otelixizumab formulation (0.2 mg/mL). The excipient levels and functionality are unique to this formulation.

TABLE 5

| Product Strength | 0.2 mg/mL mAb | | |
|---|---|---|---|
| Administration details | Dilution in normal saline required | | |

| Composition | Excipient level | Function | Additional Functionality |
|---|---|---|---|
| | 20 mM Histidine pH 6.5 | Optimal pH and buffer | Stabilizer |
| | 0.1% PS80 | Adsorption prevention to permit dosing | |
| | 10 mM Methionine | Protein antioxidant (peroxide trap) | PS80 stabilizer |
| | 0.05 mM EDTA | Protein antioxidant (metal chelator) | PS80 stabilizer |

Example 8—Comparison to Other Commercial mAb Formulations

When compared to other commercial mAbs, the otelixizumab composition presents high excipient per mAb ratio(s). See Table 6 below.

TABLE 6

| | mAb | Surfactant PS80 1 mg/mL | Antioxidant MET | Antioxidant EDTA 0.015 |
|---|---|---|---|---|
| | Otelixizumab 0.2 mg/mL 0.0014 mM | 0.7634 mM 0.1% | 1.5 mg/mL 10 mM | mg/mL 0.05 mM |
| MOLAR RATIOs | 0.02% (145 kDa) | (1310 g/mol) | 0.15% (149 g/mol) | 0.0015% (292 g/mol) |
| mAb Otelixizumab 0.2 mg/mL (145 kDa) 0.0014 mM | — | 545* | 7143* | 36 |
| Surfactant PS80 0.1% (1310 g/mol) 0.7634 mM | — | — | 13 | <1 |

*much larger than typical ratios seen in commercial mAb formulations

TABLE 7

| Commercial mAbs containing excipients of interest | | | | |
|---|---|---|---|---|
| Representative commercial biopharm products | Formulation composition | mAb | PS80 | PS80:mAb molar ratio |
| Alemtuzumab [mAb, Campath (US) Mabcampath (EU)] | Each 3 mL vial contains 30 mg alemtuzumab, 8.0 mg sodium chloride, 1.44 mg dibasic sodium phosphate, 0.2 mg potassium chloride, 0.2 mg monobasic potassium phosphate, 0.1 mg polysorbate 80, and 0.0187 mg disodium edetate dihydrate | 10 mg/mL | 0.003% | 0.4 |
| Adalimumab [mAb, Humira] | 40 mg adalimumab, 4.93 mg NaCl, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 in 0.8 mL WFI | 50 mg/mL | 0.1% | 2 |
| Tocilizumab (Actemra) | disodium phosphate decahydrate and sodium dihydrogen phosphate dehydrate (as a 15 mm/L phosphate buffer), polysorbate 80 (0.5 mg/mL) and sucrose (50 mg/mL) | 10 mg/mL | 0.05% | 3 |
| Rituximab [mAb, Rituxan] | 9 mg/mL sodium chloride, 7.35 mg/mL sodium citrate dihydrate, 0.7 mg/mL polysorbate 80, pH 6.5 | 10 mg/mL | 0.07% | 8 |
| Eculizumab [mAb, Soliris] | 0.46 mg/mL sodium phosphate (monobasic), 1.78 mg/mL sodium phosphate (dibasic), 8.77 mg/mL sodium choride, 0.22% (w/v) polysorbate 80 | 10 mg/mL | 0.22% | 25 |
| Otelixizumab [mAb] | Each mL contains 0.2 mg Otelixizumab, 2.3 mg histidine, 1.5 mg methionine, 1.08 mg histidine monohydrochloride monohydrate, 1 mg polysorbate 80, 0.015 mg disodium edetate, WFI | 0.2 mg/mL | 0.1% | 545 |

In the surfactant-containing otelixizumab formulation (0.2 mg/mL mAb and 0.1% PS80), the PS80 per mAb ratio is about 545. By comparison, Eculizumab (Soliris) which is formulated at a concentration of 10 mg/mL mAb and 0.22% PS80, the corresponding PS80 per mAb ratio is about 25. In another mAb, Rituximab, the PS80 concentration is 0.07%; thus, for a 10 mg/mL product a PS80 per mAb ratio of about 8 can be calculated. In both of these cases, the surfactant is in molar excess; however, the excess is much smaller than the ratio (545) proposed for otelixizumab. At such a large molar excess of surfactant, the purity and chemical stability of the surfactant itself needs to be considered as it is interconnected with the stability of the mAb molecule.

In the tested antioxidant-containing otelixizumab formulation (0.2 mg/mL mAb and 5 mM Met), the Met per mAb ratio was about 3,750. In the literature, an optimum ratio of 5 was reported for HER2 mAb. There are also examples of other parenteral biopharmaceutical formulations in which the Met per mAb ratio is about 100 (Follitropin alpha and beta). Although our ratio far exceeds those found in some commercial products, the higher Met concentration in our formulation may be directly correlated to the high PS80 concentration, and also the high PS80 per mAb ratio.

The material in the ASCII text file named "PU65422_US_Natl_SeqList_Sept2015 [,]" created on Sep. 10, 2015 and having a size of 6,162 bytes is incorporated herein by reference in its entirety.

What is claimed is:

1. A formulation for a therapeutic protein comprising: a) the therapeutic protein, which is an antigen binding protein or fragment thereof, at a concentration of about 0.01 mg/mL to about 1 mg/mL; b) a surfactant; and c) an antioxidant, wherein the molar ratio of surfactant to therapeutic protein is at least 100, wherein the molar ratio of antioxidant to therapeutic protein is at least 750, and wherein the antioxidant is selected from the group consisting of methionine, cysteine, glutathione, and monothioglycerol.

2. The formulation according to claim 1 wherein the molar ratio of surfactant to therapeutic protein is selected from the group consisting of at least 150, at least 200, at least 250, at least 300, at least 400, at least 500, and about 545.

3. The formulation of claim 1 wherein the surfactant is at least one selected from the group consisting of polysorbate-20, polysorbate-40, polysorbate-60, polysorbate-65, polysorbate-80, polysorbate-85 and poloxamer 88.

4. The formulation of claim 1 wherein the molar ratio of antioxidant to therapeutic protein is selected from the group consisting of at least 5500, at least 6000, at least 6500, at least 7000, and about 7143.

5. The formulation according to claim 1 wherein the formulation further comprises d) a buffer, wherein the pH of the formulation is 4.0 to 8.0.

6. The formulation according to claim 5 wherein the buffer is selected from the group consisting of histidine, acetate, citrate, and succinate.

7. The formulation according to claim 1, wherein the antigen binding protein is selected from the group consisting of an antibody, an immunoglobulin single variable domain, an anti-CD3 antibody, and an anti-CD3 antibody comprising a heavy chain comprising SEQ ID NO:1 and a light chain comprising SEQ ID NO:2.

8. A formulation for a therapeutic protein comprising: a) the therapeutic protein, which is an antigen binding protein or fragment thereof, at a concentration of about 0.01 mg/mL to about 1 mg/mL; and b) 0.01% w/v to 0.5% w/v surfactant, wherein the molar ratio of surfactant to therapeutic protein is at least 100; c) 1 mM to 50 mM antioxidant, wherein the molar ratio of antioxidant to therapeutic protein is at least 750; and d) 1 mM to 100 mM buffer, wherein the pH of the formulation is 4.0 to 8.0.

9. The formulation of claim 8 wherein the therapeutic protein is an antibody, wherein the surfactant is polysorbate 80, wherein the antioxidant is methionine, and wherein the buffer is histidine.

10. The formulation according to claim 1, wherein the therapeutic protein is present at a concentration of about 0.1 mg/mL to about 0.5 mg/mL.

11. The formulation according to claim 1, wherein the therapeutic protein is present at a concentration of about 0.2 mg/mL.

12. The formulation according to claim 1, wherein the formulation further comprises 0.01 mM to 1.0 mM EDTA.

13. The formulation according to claim 1, wherein the formulation further comprises 0.01 mM to 0.1 mM EDTA.

14. The formulation according to claim 1, wherein the formulation further comprises 0.05 mM EDTA.

* * * * *

SEQUENCE LISTING

```
<160> NUMBER OF SEQ ID NOS: 2

<210> SEQ ID NO 1
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 216
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Gln Leu Thr Gln Pro Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
            35                  40                  45

Ile Tyr Asp Asp Asp Lys Arg Pro Asp Gly Val Pro Asp Arg Phe Ser
50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                    85                  90                  95

Ser Phe Asn Val Phe Gly Gly Gly Thr Lys Leu Thr Val Leu Arg Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
        195             200             205

Thr Val Ala Pro Thr Glu Cys Ser
    210             215
```